United States Patent [19]

Fujiwara

[11] 4,420,384

[45] Dec. 13, 1983

[54] METHOD FOR DETERMINING BOUNDARY POINTS ON ELECTROPHORETIC PATTERNS AND MEANS THEREFOR

[75] Inventor: Toshihide Fujiwara, Hachiouji, Japan

[73] Assignee: Olympus Optical Co., Ltd., Tokyo, Japan

[21] Appl. No.: 292,537

[22] Filed: Aug. 13, 1981

[30] Foreign Application Priority Data

Aug. 22, 1980 [JP]  Japan ................................ 55-115659

[51] Int. Cl.³ ............................................ G01N 27/26
[52] U.S. Cl. ............................ 204/180 G; 204/180 S; 364/416; 364/498
[58] Field of Search ............... 204/180 S, 180 G, 301; 364/416, 498

[56] References Cited

U.S. PATENT DOCUMENTS 4,242,730  12/1980  Golias et al. ....................... 364/416
4,295,949  10/1981  Fujiwara et al. ................ 204/180 G
4,312,728  1/1982  Kamachi et al. ................ 204/180 G Primary Examiner—John F. Niebling
Attorney, Agent, or Firm—Cushman, Darby & Cushman

[57] ABSTRACT

A method for determining boundary points on electrophoretic patterns whereby boundary points can be easily and accurately added onto or erased from fractionated patterns or analogue patterns by utilizing a densitometer for obtaining fractionated patterns of serums formed by an electrophoresis, a computer for making necessary operations and data treatments, an input terminal device for putting boundary point position informations or the like into the computer and an output terminal device which can record and digitally type analogue patterns with the output of the computer and means for working the method. Any input error by the input terminal device can be corrected.

2 Claims, 8 Drawing Figures

FIG. 3
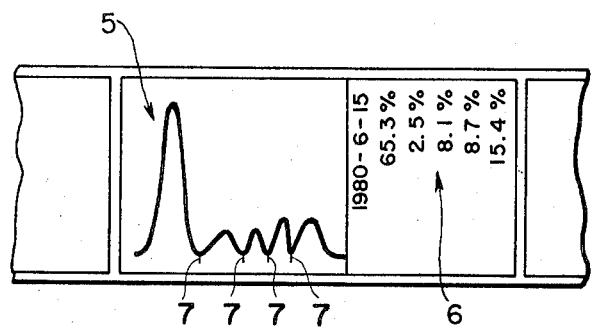
FIG. 4
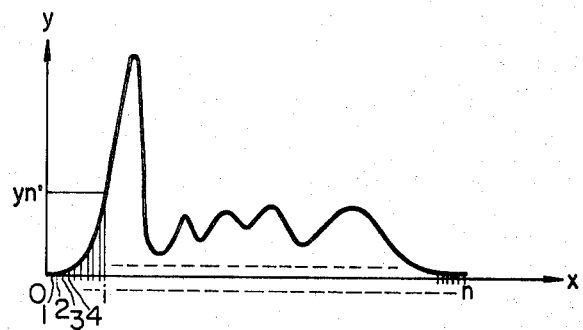
FIG. 5
| ADDRESS | BOUNDARY POINT INFORMATION BIT | DATA |
|---|---|---|
| $\alpha$ | 0 | $y_0$ |
| $\alpha+1$ | 0 | $y_1$ |
| $\alpha+2$ | 0 | $y_2$ |
| $\alpha+3$ | 1 | $y_3$ |
| $\alpha n'$ | 1 | $y_{n'}$ |
| $\alpha_{n-1}$ | 0 | $y_{n-1}$ |
| $\alpha n$ | 0 | $y_n$ |

METHOD FOR DETERMINING BOUNDARY POINTS ON ELECTROPHORETIC PATTERNS AND MEANS THEREFOR

BACKGROUND OF THE INVENTION a. Field of the Invention

This invention relates to a method for determining boundary points on analogue patterns based on fractionated patterns obtained by electrophoresizing serums and means for working the method.

b. Description of the Prior Art

Generally, in the electrophoresis, an analogue pattern is determined by measuring with a densitometer fractionated patterns obtained by electrophoresizing a sample or serum. This analogue pattern is generally in such form as is shown in FIG. 1. That is to say, the standard analogue pattern is divided into an albumin fraction $A_1$ having a peak $a_1$, an $\alpha_1$ globulin fraction $A_2$ having a peak $a_2$, an $\alpha_2$ globulin fraction $A_3$ having a peak $a_3$, a $\beta$ globulin fraction $A_4$ having a peak $a_4$ and a $\gamma$ globulin fraction $A_5$ having a peak $a_5$, the respective boundary points $b_1$, $b_2$, $b_3$ and $b_4$ of the fractions $A_1$, $A_2$, $A_3$, $A_4$ and $A_5$ are set respectively in the valleys of the analogue pattern and the values in % or the like of the areas of the respective fractions $A_1$, $A_2$, $A_3$, $A_4$ and $A_5$ are determined. The determination of such boundary points and the calculation of the values in % or the like of the respective fractions are automatically made with a computer on the basis of data obtained by measuring the fractionated patterns of the sample with a densitometer.

FIG. 1 is a view for explaining the summary of a conventional method for determining boundary points with a computer. As shown in FIG. 1, points $x_1$, $x_2$, ... are provided at fixed intervals of $\Delta x$ along the abscissa from the starting point in an electrophoretic pattern, the densities (the values of y in the electrophoretic pattern) $y_1$, $y_2$, ... of the fractionated patterns at these points $x_1$, $x_2$, ... are measured and such value $y_b$ as satisfies the relations of $y_{b-1} > y_b$ and $y_b < y_{b+1}$ is determined. The point $x_b$ on the abscissa corresponding to this $y_b$ is of the value on the ordinate X of the boundary point b. This will be able to be realized when the fractionated patterns of the sample are scanned with the densitometer, the continuously obtained measured values are memorized at intervals of the time corresponding to $\Delta x$, the time point satisfying the above described conditions is memorized and, at the same time, marks showing the boundary points are attached to the parts of the valleys of the analogue pattern while being recorded, for example, on a recording sheet.

Now, some sample is proper to be treated with other positions than the positions of the valleys of the above mentioned analogue pattern as boundary points. Further, when no valley is present in the position which should be inherently a boundary point, the mark showing the boundary point will not be automatically attached but, in some case, a boundary point will have to be newly set in this position. In order to cope with such case, there is required a means whereby the operator can erase or set the boundary point as required and a required calculation can be automatically made accordingly.

The following means which can meet such requirements are already known.

One of them is a system wherein fractionated patterns are measured with a densitometer and, while an analogue pattern is being described on the basis of the fractionated patterns, the moment the point wanted to be a boundary point is recorded, a switching device will be operated to set the boundary point and to thereby make the fractionation. Therefore, the means of this system is so designed that the recording speed is lower than usual and the fractionation can be accurately made. However, in this system, there are defects that the operation of setting the boundary point must be made while the analogue pattern is being described, therefore the boundary point can not be set under the general judgment by seeing the completed entire analogue pattern and it is difficult to judge the position of the boundary point wanted to be set. Further, in case the setting of a proper boundary point fails, it will not be able to be erased and therefore no failure will be allowed. Further, as the boundary point must be set while the analogue pattern is being described, it is so difficult to set the boundary point in an accurate position as to require a skill.

Another conventional example is a system wherein an already described analogue pattern is set in a predetermined place in a means, a slider fitted movably in the means is moved on the above mentioned set analogue pattern as synchronized with the record of the analogue pattern based on the measurements of the fractionated patterns and, when the slider comes to the position to be fractionated, a boundary point setting button will be pushed to set a new boundary point. Even in this system, there is a defect that, when the boundary point setting button is pushed, no erasing will be able to be made. Further, though this sysem is easier to set the boundary point than the above mentioned first conventional example, there is a defect that, as the boundary point is set while the slider is moving, it can not be accurately set.

SUMMARY OF THE INVENTION

An object of the present invention is provide a method and apparatus for determining boundary positions on electrophoretic patterns wherein such defects of conventional systems as are mentioned above are eliminated and the positions of the boundary points can be easily and accurately set.

According to the present invention, this object is attained by providing a step wherein a densitogram is obtained from fractionated patterns formed by an electrophoresis, a step wherein data obtained by sampling this densitogram and boundary point informations corresponding to the respective data are memorized by a computer and a step wherein the informations of erasing boundary points or setting new boundary points are put into the computer by a terminal device on the basis of the same analogue pattern as of the above mentioned data memorized by the computer so that the boundary point information memorized by the computer can be altered.

According to a preferred formation of the present invention, there are provided a densitometer device for obtaining a densitogram from fractionated patterns formed by an electrophoresis, a computer for memorizing and treating data obtained by the densitometer device and a terminal device which can put the informations of erasing boundary points or setting new boundary points into the computer.

The terminal device includes a clear key which can erase any erroneous information when put into the computer so that the input information may be immediately corrected or altered.

According to the present invention, there is provided an output terminal device which is connected to the computer and can record and digitally type an analogue pattern on the basis of an output of the computer.

This and other objects of the present invention will become more apparent during the course of the following detailed description and appended claims.

BRIEF DESCRIPTION OF THE DRAWINGS

FIG. 3 is a view showing an analogue pattern before a new boundary point is set;

FIG. 4 is a view for explaining a method of sampling an analogue pattern;

FIG. 5 is a view showing data as memorized in a memory;

DESCRIPTION OF THE PREFERRED EMBODIMENTS

Figure 1:
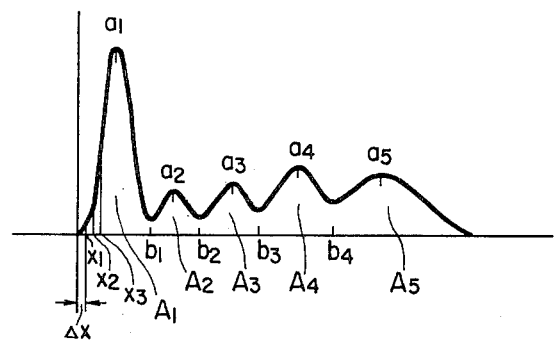
FIG. 1 is a view showing a standard analogue pattern of fractionated patterns.
Figure 2:
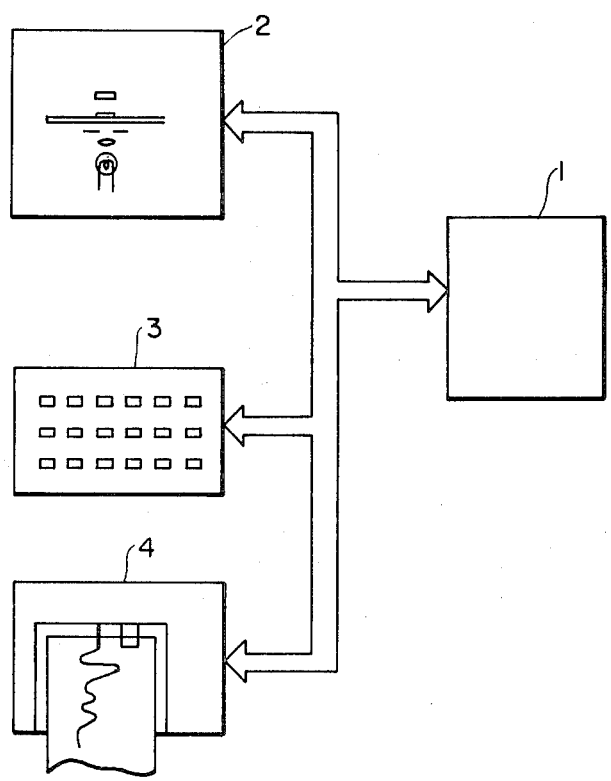
FIG. 2 is a block diagram of an apparatus to be used to work the method of the present invention.

The detailed contents of the present invention shall be explained in the following on the basis of the drawings. FIG. 2 is a block diagram showing the formation of an apparatus to be used to work the present invention. The reference numeral 1 denotes a computer by which the below described respective devices are controlled and necessary operations and data treatments are made, 2 denotes a densitometer for measuring fractionated patterns formed by an electrophoresis, the data obtained here being sent to the computer, 3 denotes an input terminal device for putting in boundary point position informations or the like and 4 denotes an output terminal device in which an analogue pattern is recorded and digitally typed.

In such formation as in the above, first an analogue pattern obtained by the densitometer 2 is recorded by a recorder and the analogue pattern data are memorized in a memory. That is to say, on the recording sheet, such analogue pattern 5 as is shown in FIG. 3 is recorded and the values in % or the like of the respective fractions are typed as shown by the reference numeral 6. Here, boundary point marks are attached as shown by the reference numeral 7 to the parts to be boundary points on the analogue pattern. The analogue signals of the fractionated patterns are A/D converted and are memorized in the CPC memory. In this case, as shown in FIG. 4, the analogue signals are sampled and A/D converted at fixed time intervals and the digital values are memorized. That is to say, as shown in FIG. 4, if sampling points (0, 1, 2, ... i ... n) are taken on the abscissa x and the pattern densities corresponding to the sampling points are taken on the ordinate y, the value of y corresponding to the point x will be memorized in the memory. FIG. 5 shows the values of y as memorized in the memory. $\alpha$, $\alpha+1$, ... $\alpha_n$ denote addresses of the memory. $\alpha$ corresponds to $x=0$ and $\alpha_n$ corresponds to $x=n$. The density values y ($y_0$, $y_1$, $y_2$, ...) corresponding to the respective addresses are memorized respectively in the addresses. Further, in the data of the boundary points, 1 is set at the boundary point information bit and others than the boundary point are made 0.

Next, when the boundary point is wanted to be erased or added, the boundary point information is put in from the input terminal device 3. The boundary point information consists of a boundary point erasing information and a boundary point adding information. Only one of these two informations or both of them may be put in. The boundary point erasing information of these informations is used, for example, in the case that an abnormal fraction is present in the analogue pattern, is a boundary point and is to be erased. The boundary point adding information is used, for example, in the case that no fraction is present at the point to be a boundary and a boundary point is to be newly provided.

The method of erasing the boundary point information shall be first described. When the key (for example, a minus "−" symbol is attached to this key) of the boundary point erasing information and the key, for example, "2" of the numeral showing what number boundary point from the side (starting side) of the peak value of albumin the boundary point wanted to be erased is pushed, the boundary point second from the peak value of albumin will be thereby erased.

Figure 6:
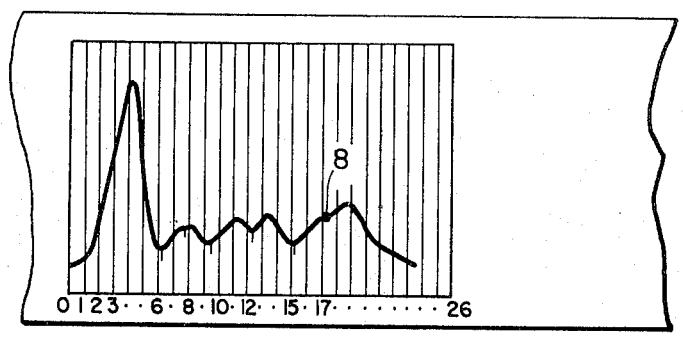
FIG. 6 is a view showing an analogue pattern described on a recording sheet on which a boundary point setting scale is printed.

Now, the case of putting in the boundary point adding information shall be described. In the case that the key (marked, for example, with "+") of the boundary point adding information is pushed and an analogue pattern is recorded on a recording sheet on which a scale is printed as shown in FIG. 6, the position of the boundary point to be added is read with the scale. For example, in case the point indicated by the numeral 8 is to be made a boundary point, "17.1" is put in. In the case that an analogue pattern is to be recorded on a recording sheet on which no scale is printed as in FIG. 7, the length l on the abscissa x between the recording starting point 0 and the boundary point to be added is measured and the value is put in.

In the above method, such key as, for example, the "−" key or "+" key is used to indicate whether the information is for the erasion or addition. However, the input data themselves may include a signal for the erasion or addition so as to be treated without using the key for the erasion or addition. For example, at the time of the erasion, "0" is put into each of the upper two figures for distinction. That is to say, in case the above described boundary point second from the peak position of albumin is wanted to be erased, "002" may be put in.

In case any input error is noticed during the input, the input may be cleared with the clear key "CE" or the like and then such correction as putting in again may be made.

When the boundary point information has been thus put in, for example, the "END" key or "START" key is pushed to proceed to the next step. That is to say, by the input information, the information memorized in the memory may be altered (corrected). Next, the concrete contents shall be explained in the following.

First, the case that the boundary point erasing information is put in shall be explained. The data measured with the densitometer 2 have been memorized in the memory as shown in FIG. 5. In case such boundary point erasing information as, for example, the above described "−" and "2" are put into them, the "1" appearing for the second time when the boundary point information bits are examined in turn from the addresses of the albumin fractions will be canceled to be made "0". Therefore, if the analogue pattern is recorded on the basis of the data memorized in this memory, it will be recorded without attaching the boundary point mark 5 to the second minimum value. Further, also, in the case that the % values or the like of the respective fractions are to be determined with the computer 1, the respective values calculated without making the second minimum value a boundary point will be typed.

Next, the case that the boundary point adding information is put in shall be described. As described above, the analogue pattern is obtained by D/A converting the digital value data put out at fixed time intervals when the electrophoretic pattern is measured with the densitometer 1. Therefore, the length (on the abscissa x) of the analogue pattern is determined by the time intervals of putting out in turn the memorized data and the recording sheet feeding speed. That is to say, if the time intervals at which the digital value data are put out and the recording sheet feeding speed are constant, the number of the output data and the length of the analogue pattern will correspond to each other at a ratio of 1 to 1. Therefore, now, if the length to the abnormal boundary point on the analogue pattern is l, the address of the light measurement starting point is $\alpha$ and the address of the xth data is $\alpha_x$, the relation of $(\alpha_x - \alpha) = kl$ wherein k is a constant will hold. Therefore, in the case of the above described example in which the length to the abnormal boundary point is 17.1, the boundary point adding informations "+" and "17.1" will be put in. That is to say, as $\alpha_x = \alpha + k \times 17.1$ from $(\alpha_x - \alpha) = k \times 17.1$, $\alpha_x$ is determined from this and the boundary point information bit of the determined $\alpha_x$ is set at "1". Thereby, if the analogue pattern is recorded again on the recording sheet, the mark of the boundary point will be recorded in the place (not of the minimum value) of the length of 17.1. In the same manner, the % values or the like will be typed with this point as a boundary point.

Figure 7:
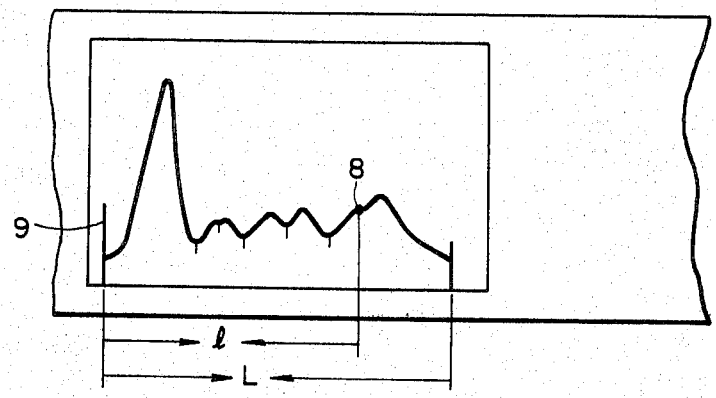
FIG. 7 is a view showing a method of setting boundary points of an analogue pattern described on a recording sheet on which no scale is printed.

Here, due to the relation of the recording sheet feeding speed with the precision or the like, the address $\alpha_x$ may be different. In order to eliminate this difference and to make a fractionated result higher in the precision, that is, to elevate the precision of the boundary point position, there is a method wherein, as shown in FIG. 7, the mark 9 which will be a standard in the case of measuring with the scale, that is, the mark of the starting point is put in or, at the time of the input of the data, the length to the added point and simultaneously also the total length from the start to the end point of the analogue pattern are put in and the ratio of them is determined to determine the position wanted to be made a boundary point. In the case of the method by such ratio, when the length to the added boundary point is l, the total length is L and the address of the end point is $\alpha_n$, the address $\alpha_x$ of the added boundary point may be calculated from the following relation and the boundary point information bit of this address may be made 1:

$$\frac{\alpha_x - \alpha}{\alpha_n - \alpha} = \frac{l}{L}$$

According to this method, the time intervals of the data output and the recording sheet feeding speed can be neglected.

Figure 8:
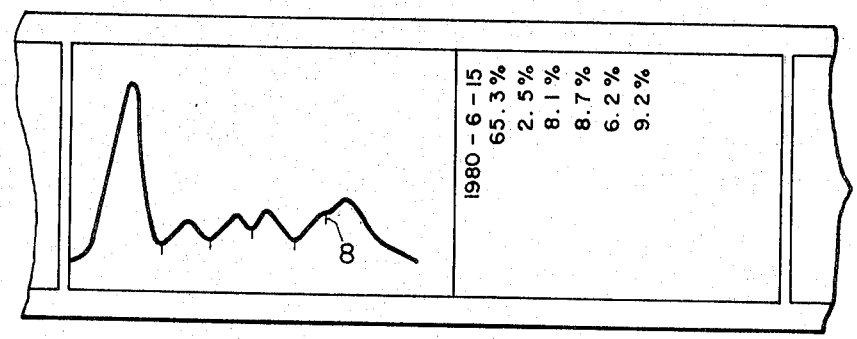
FIG. 8 is a view showing an analogue pattern recorded after a boundary point is set.

After the new boundary point is set as in the above, the data may be treated as usual. That is to say, the value at the boundary point newly reset on the basis of the data memorized in the computer 1 is calculated with the computer and, on the recording sheet, an analogue pattern (on which the mark of the new boundary point is shown) is described and the % value of the fraction is typed. In FIG. 8, there are shown a newly recorded analogue pattern on which the new boundary point 8 is marked and the final output in which such data as the % value of the new fraction are typed.

By the way, in case the analogue pattern is used to set a boundary point, the % value of the fraction will not be required to be typed. Therefore, the first recording may be only of the analogue pattern and the fraction value or the like may not be typed.

According to the method of setting boundary points of the present invention as explained above, only a simple input operation by the input terminal device will do and therefore no special device will be required. Further, after the analogue output ends, that is, after the analogue pattern is recorded, the boundary point is set (erased and added). Therefore, after the general judgment is made in the light of the entire analogue pattern, the boundary point can be determined. Further, the boundary point setting operation is not operatively connected with the sequence operation and therefore is not restricted in the time and anyone can easily and accurately determine the boundary point. Further, any error noticed during the input can be corrected.

I claim:

1. A method for determining boundary points on electrophoretic patterns, comprising a step wherein a densitogram is obtained from fractionated patterns formed by an electrophoresis, a step wherein the data obtained by sampling from said densitogram and the boundary point information determined on the basis of said data are memorized in a computer, and a step wherein the boundary point erasing or new boundary point setting information is put into said computer by a terminal device on the basis of an analogue pattern obtained from said fractionated patterns to alter the boundary point information memorized in said computer, a boundary point being put into said computer on the basis of an input distance information when the boundary point is to be added, and the boundary point being erased by putting the address number of the boundary point into said computer when the boundary point is to be erased.

2. A method according to claim 1, further comprising a step wherein an analogue pattern is recorded and digitally typed on the basis of the output of said computer.

* * * * *